United States Patent [19]
Joshi et al.

[11] Patent Number: 5,021,137
[45] Date of Patent: * Jun. 4, 1991

[54] CERAMIC SOLID ELECTROLYTE BASED ELECTROCHEMICAL OXYGEN CONCENTRATOR CELL

[75] Inventors: Ashok V. Joshi; Mustafa B. Syammach, both of Salt Lake City; Scott S. Campbell, West Valley City, all of Utah

[73] Assignee: Ceramatec, Inc., Salt Lake City, Utah

[*] Notice: The portion of the term of this patent subsequent to Nov. 7, 2006 has been disclaimed.

[21] Appl. No.: 432,919

[22] Filed: Nov. 6, 1989

Related U.S. Application Data

[63] Continuation-in-part of Ser. No. 156,549, Feb. 16, 1988, Pat. No. 4,879,016, which is a continuation-in-part of Ser. No. 889,214, Jul. 25, 1986, Pat. No. 4,725,346.

[51] Int. Cl.$^5$ ............................ C25B 1/02; C25B 9/00
[52] U.S. Cl. ................................... 204/242; 204/129; 204/130; 204/153.18; 204/265; 204/266; 204/421; 204/424
[58] Field of Search .................... 204/153.18, 421–429, 204/129, 130, 242, 263, 265, 266

[56] References Cited

U.S. PATENT DOCUMENTS

| | | | |
|---|---|---|---|
| 3,481,855 | 12/1969 | Kolodney et al. | 204/422 |
| 3,922,204 | 11/1975 | Tseung et al. | 204/1 S |
| 4,257,863 | 3/1981 | Hoffman | 204/429 |
| 4,283,441 | 8/1981 | Haecker et al. | 204/424 |
| 4,359,374 | 11/1982 | Sano et al. | 204/429 |
| 4,412,904 | 11/1983 | Rohr et al. | 204/424 |
| 4,547,281 | 10/1985 | Wang et al. | 204/426 |
| 4,610,867 | 9/1986 | Seiyama et al. | 204/424 |
| 4,720,335 | 1/1988 | Fukishima et al. | 204/424 |
| 4,725,346 | 2/1988 | Joshi | 204/130 |
| 4,879,016 | 11/1989 | Joshi | 204/424 |

Primary Examiner—T. Tung
Attorney, Agent, or Firm—Trask, Britt & Rossa

[57] ABSTRACT

The invention is a ceramic solid electrolyte based electrochemical oxygen concentrator cell and the method for fabricating said cell. The cell is based on a doped cerium oxide ceramic solid electrolyte and lanthanum strontium cobaltite ceramic electrodes.

7 Claims, 5 Drawing Sheets

CERAMIC SOLID ELECTROLYTE BASED ELECTROCHEMICAL OXYGEN CONCENTRATOR CELL

RELATED APPLICATIONS

This application is a continuation-in-part of U.S. patent application Ser. No. 156,549, filed on Feb. 16, 1988, now U.S. Pat. No. 4,879,016, which was a continuation in part of U.S. patent application Ser. No. 889,214, filed July 25, 1986, now U.S. Pat. No. 4,725,346.

This application is being filed concurrently with U.S. patent application Ser. No 432,523, now abandoned, in the names of Stuffle, Nachlas and Joshi. The contents of such concurrently filed application and U.S. Pat. Nos. 4,725,346 and 4,879,016 issued to Joshi are incorporated herein by reference, all of which, including this application, have a common assignee.

BACKGROUND OF THE INVENTION

1. Field

This invention generally relates to oxygen generating devices and particularly to electrochemical oxygen generating devices using metal oxide, oxygen ion conducting electrolyte.

2. State of the Art

Electrochemical devices which employ oxygen ion conducting electrolytes are well known. Such devices are used as sensors whereby the oxygen partial pressure difference existing between opposite sides of said electrolyte create a voltage potential which may be determined to indicate a level of oxygen concentration on one side or the other, especially when the oxygen concentration on one side of the sensor is known. Such sensors are used in automobile engines, furnaces and other devices wherein it is desired to operate at stoichiometric ratios between the fuel and the air or oxygen necessary for combustion of fuel.

Also, such electrochemical devices, when operated in a current mode with an applied voltage may be utilized to generate pure oxygen. Devices of this type are discussed in certain patents to Ruka, for example, Re. 28,792.

Certain difficulties have generally been encountered with such oxygen sensors and oxygen generating devices. In electrochemical sensors it is common practice to utilize platinum as an electrode or to utilize various electrode layers, for example, a platinum electrode adjacent to the electrolyte with an overcoating of a protective porous film. Platinum has been generally employed because of its catalytic activity and because of its relatively high melting point among conductive metals. It has been found, however, that the use of platinum in oxygen generating electrochemical cells that the platinum, which is relatively conductive, has an apparent resistance higher than what would normally be expected. Thus, oxygen generating electrochemical cells utilizing platinum electrodes have been electrically inefficient. Furthermore, since the platinum electrodes must be porous in order to permit oxygen molecules to reach the surface of the electrolyte at the cathodes, and, upon recombination at the anode surface, to depart from the electrolyte. While pores are thus necessary, the effective electrode-electrolyte interface for electrical purposes is consequently reduced.

Sensors generally are quite small, frequently formed as a disk smaller than a dime or as a thin thimble having a length of about one-half inch and an outside diameter of less than one-fourth inch. The amount of voltage or current applied or produced by sensors is very small, generally being in the millivolt and milliamp range. The problems of uniform current distribution over a broad area is generally not encountered because of the small size of the device.

The aforementioned patents of Joshi describe many of the considerations involved in producing useful oxygen delivery devices and further describe certain advantageous electrode/electrolyte systems.

Sensors are produced to maximize response time, to endure repeated hot/cold cycling, to be reliable over an extended period of time. Maximizing the quantity of oxygen transported through the electrolyte per amp applied is generally not a factor in sensor design or fabrication.

An oxygen delivery device, while employing oxygen conducting electrolytes and current carrying electrodes, has different objectives than a sensor and involves different considerations. An oxygen delivery device employing larger electrolytes has a very large surface area in comparison to a sensor. Because of the size of the electrolyte, strength is an important factor. Also, the problems of differential temperatures may create stress problems, especially if an area of an electrolyte begins conducting more oxygen ions than other areas, which results in hot spots. A hot spot may be a result of uneven distribution of current by the electrode or a thin wall spot on the electrolyte.

While platinum has generally been the standard electrode for zirconia-type sensors, its use in oxygen delivery devices has been generally unsatisfactory.

SUMMARY OF THE INVENTION

The instant invention relates to an oxygen delivery device having exceptional oxygen-producing capacity per unit area of electrolyte. A unique aspect of the invention involves an electrolyte assembly comprising a doped cerium oxide (ceria) electrolyte in combination with a pervoskite material electrode, especially lanthanum strontium cobaltite. Preferably, the pervoskite electrode has an overlayer of silver to enhance operation at low temperatures, i.e., less than about 800° C.

The oxygen delivery devices of this invention are solid state electrochemical cell having air on the cathode side of the electrolyte so that under the influence of a direct current, oxygen ions are transported through the electrolyte to be released (pumped) at the anode as oxygen gas.

This invention has performance characteristics that far exceed the existing oxygen concentrator cell system based on doped zirconium oxide ceramic electrolyte and lanthanum strontium manganite ceramic electrodes. The performance of electrochemical oxygen delivery cells is characterized by the current density of the cell at set voltages and temperatures during operation and the faradaic efficiency, a measure of cell oxygen pumping efficiency. An existing cell employing a zirconia electrolyte operates at a current density of 115 mA/cm$^2$ at a faradaic efficiency of 100% at 800° C. and 1.0 volts dc bias potential. Cells fabricated with the materials and method of this invention exhibit a current density of 450 mA/cm$^2$ and 100% faradaic efficiency at 800° C. and 1.0 volt dc bias, a current density 290% greater than obtained with the existing cell.

Electrochemical oxygen delivery cells produced with this invention exhibit oxygen pumping performances far greater than obtained with existing systems.

DETAILED DESCRIPTION OF THE ILLUSTRATED EMBODIMENT

Ceramic solid electrolyte based electrochemical oxygen concentrator cells (SEOC), also referred to as delivery devices, are used for the production of oxygen concentrators producing high purity oxygen. The concentrators separate oxygen from ambient air to supply a flow of 99% pure oxygen. These concentrators are being produced for use in the medical, aerospace, defense, semiconductor, and utilities industry. The advantage of solid electrolyte base electrochemical oxygen concentrators over the existing pressure swing adsorption systems (PSA) are 1) production of higher purity oxygen (>99% for electrochemical based systems as opposed to <95% for PSA based systems), 2) lower maintenance requirements (once per year for electrochemical systems as opposed to 4 times per year for PSA systems), 3) simplicity of operation, 4) weight, and 5) size.

The basis of operation of SEOC's is the oxygen ion conductivity of the ceramic solid electrolyte. The ceramic solid electrolyte generally used for the production of SEOC cells is zirconium oxide doped with yttrium oxide and ytterbium oxide. This material is a pure oxygen ion conductor implying that the charge carrier used in electrical current flow are oxygen ions as opposed to electrons, the charge carrier for electronically conductive materials. The oxygen ion conductivity of doped zirconium oxide is highly temperature dependent, thus the material must be heated to temperature greater than 700° C. before appreciable oxygen ion conductivity is achieved. The normal operating temperature of SEOC cells using zirconium dioxide electrolyte is 800° C. or more.

Figure 1:
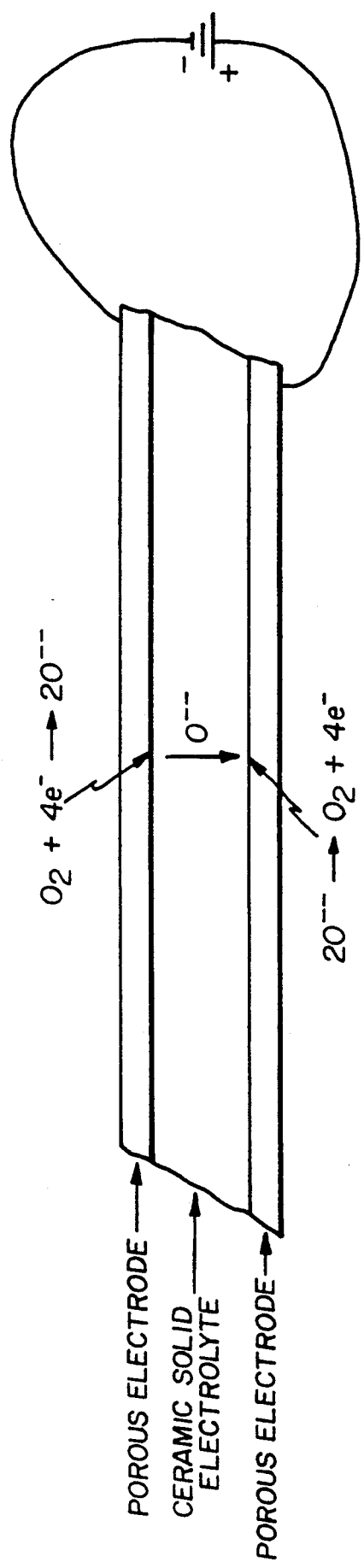
FIG. 1 is a schematic view of an electrolyte assembly of an electrochemical oxygen generating device.

For the SEOC cell to function, an electronically conductive material (electrode) must be applied to the electrolyte material to provide an interface where gaseous oxygen molecules can pick up electrons and be "ionized" to provide oxygen ions for conduction. An interface of this nature must also be present on the other side of the electrolyte to facilitate the removal of electrons form the oxygen ions to produce oxygen molecules. A schematic illustrating this concept is shown in FIG. 1. At present, an especially suitable electrode material for this purpose is a porous lanthanum strontium manganite ceramic. This material has a relatively high electronic conductivity as well as high catalytic activity for oxygen. This ceramic material is also chemically and mechanically compatible with doped zirconium dioxide ceramic solid electrolytes. The pores within such an electrode material permit gaseous oxygen to be present at the electrode/electrolyte interface.

As shown in FIG. 1, a dc voltage bias is applied across the ceramic electrolyte via the electrode material at high temperatures. In the presence of an oxygen containing gas such as air, oxygen ions are conducted through the electrolyte material and recombine to form pure oxygen on the other side. As shown in FIG. 1, the ceramic solid electrolyte cell is in a tubular form with one closed end to facilitate manifolding.

Two critical parameters are measured when evaluating the performance of a SEOC cell. These parameters are 1) the current density and 2) the faradaic efficiency. The current density (measured in $mA/cm^2$) is a measure of the amount of current that passes through a unit active area of the cell. The current density is a function of the ion conductivity of the electrolyte, the electrical conductivity of the electrode, and the catalytic activity of the electrode/electrolyte interface. The current density of a cell increases with increases in all the above parameters. The current density is measured by measuring the amount of current that passes through a known active area of the cell at a specific temperature and applied dc voltage. In the case of evaluating SEOC cells, the chosen temperature is 800° C. and the chosen dc voltage is 1.0 volts. Such parameters are important in defining the amount of active cell area and electrical power required to produce a desired flow rate of pure oxygen. The higher the current density the more desirable the system for SEOC applications. An existing system based on zirconium dioxide base electrolytes yield a current density of 115 $mA/cm^2$ at 800° C. and 1.0 volts bias. The minimum requirement for commercial application of SEOC cells is a current density of 100 $mA/cm^2$. Higher values are more desirable.

The second critical parameter is the faradaic efficiency (expressed in $cm^3/min/amp$). The faradaic efficiency is a measure of the amount of oxygen flow produced by each amp of current passing through a SEOC cell. For the case of an SEOC cell operating at sea level ambient pressure and delivering room temperature (25° C.) oxygen to the flow measurement system, the faradaic efficiency is 3.8 $cm^3/min/amp$ when all of the current flowing through the SEOC cell is due to the conduction of oxygen ions. In this case, the faradaic efficiency is said to be 100%. A faradaic efficiency of 100% is required for SEOC cells as this would indicate that all of the current passed goes to separating oxygen from air and thus has a 100% electrical efficiency. This is the case for SEOC cells based on the existing zirconium dioxide ceramic electrolyte system.

The invention relates to the composition and method of fabrication for producing SEOC cells based on a calcium oxide doped cerium oxide solid electrolyte and a lanthanum strontium cobaltite ceramic electrode. SEOC cells produced using this invention exhibit a current density of 450 $mA/cm^2$ and a faradaic efficiency of 3.8 $cm^3/min/amp$ at 800° C. and 1.0 volts dc operating voltage. This current density exceeds the current density of the zirconia-based SEOC system by 290%. Thus, an electrolyte assembly comprising a doped ceria electrolyte in conjunction with a lanthanum strontium cobaltite electrode is a more desirable system for the production of SEOC units since such a high current density implies a reduction in size and power consumption of a unit relative to units based on a zirconia-based system.

EXAMPLE

The first procedure in fabricating SEOC cells using this invention is to fabricate cell tubes out of CaO doped cerium oxide electrolyte material. The starting material is a powder prepared in the following manner. Calcium carbonate and cerium oxide powders are weighed to create a composition in the region of 0.5-20.0 m/o CaO and 99.5-80.0 m/o cerium oxide then placed in a ball mill for mixing. The ball mill contains zirconium oxide milling media and water containing a dispersant. The amount of water is kept to a level whereby the slurry formed during mixing is 80% solids. The materials are mixed for 2-4 hours before being poured into heated trays for drying.

After drying, the resultant powder cake is pulverized and passed through a 40 mesh sieve. The sieved powder is placed into aluminum oxide crucibles and prereacted at temperatures between 1200° and 1350° C.

After firing, the prereacted powder is ball milled to reduce its particle size in a plastic ball mill containing zirconium oxide milling media and enough water to produce a slurry containing 67% solids. The material is milled for 16 hours before a ceramic binder material is added in a proportion of 1-3 w/o. The milling is continued for one more hour before the slurry is poured into heated trays for drying.

After the material is dried, it is crushed and passed through a 40 mesh sieve. After sieving, the material is placed into an isostatic pressing die to form a closed ended tube 12" long by ½" in diameter. The pressing pressure is between 15,000 and 30,000 psi and maintained for 1-3 minutes.

After pressing, the green tubes are placed on aluminum oxide setters covered with a bed of cerium oxide powder. The layer of cerium oxide powder is used to prevent a reaction from occurring between the tubes and the setter. The setter and tubes are placed in a high temperature furnace and fired at a heating rate between 50 and 100° C./min to 1400°-1600° C. and held at temperature for 2-5 hours.

After firing, tubes are inspected for defects and density and are ready for the electrode application process.

The lanthanum strontium cobaltite (LSC) ceramic electrode material is prepared using the same mixing and milling procedures as above. Lanthanum carbonate, strontium carbonate, and cobalt oxide are weighed in such proportions to yield a final composition of 0.10-0.40 m/o lanthanum oxide ($La_2O_3$), 0.20-0.80 m/o strontium carbonate, and 1.0 m/o cobalt oxide. The prereaction temperature used is between 900° and 1100° C. for 2-6 hours. The particle size reduction milling procedure is for 24 hours and uses ethanol instead of water. No binders are added during this procedure.

After milling and drying, a paste is prepared using the resultant powder and a composition containing 32-40 w/o polyvinyl butylral (PVB) binder and 60-68 w/o terpineol solvent. The solids content is 50-60 w/o. The paste is prepared by stirring the LSC ceramic electrode powder into the binder/solvent mixture with a 1-10 w/o addition (based on solids) of cerium oxide for fifteen minutes with a plastic spatula in a glass jar. The cerium oxide acts as a binding agent between the ceramic electrode and electrolyte during firing. The LSC electrode paste is stored in a seal glass jar.

Figure 2:
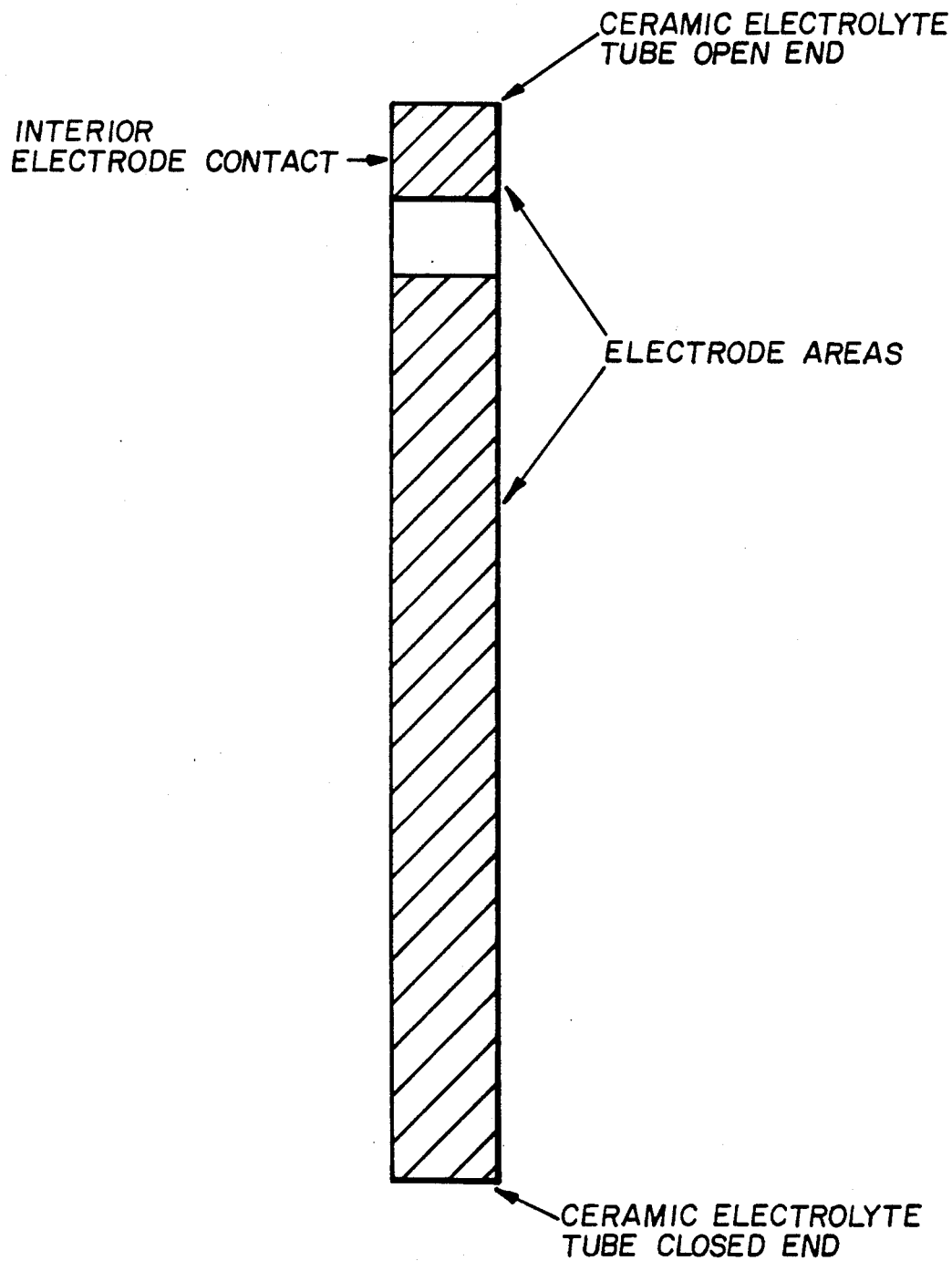
FIG. 2 is an elevational view of a tubular ceramic electrolyte.

The LSC paste is applied to the cerium oxide ceramic electrolyte tube using a paint brush on the exterior in the pattern shown in FIG. 2. This is followed with several passes of a cotton swab to even distribute the paste on the interior surface.

After LSC electrode paste is applied to both the exterior and interior surfaces of the tube, the paste is dried in an inverted position by heating the tube with a heat gun. After drying, the tubes are placed in a furnace and fired to a temperature between 1000° and 1200° C. for 1-4 hours to form the electrode/electrolyte interface and bond the LSC electrode material to the cerium oxide ceramic electrolyte tube.

The electrode paste application, firing procedures are repeated until four layers of LSC electrode material have been applied. A typical LSC electrode applied in this manner has a thickness of about 100 microns±30 microns.

Once four layers of LSC material have bee applied, a layer of silver paste is applied to both interior and exterior surfaces in the manner described above, and fired to a temperature between 700° and 850° C. for 1-2 hours. The silver layer is applied to the serve as a current collecting electrode to apply current evenly over the entire area when a voltage is applied during operation.

Once the silver layer has been applied and fired, the cell is ready for operation. The silver layer is generally about 5 to 15 microns in thickness and at such thicknesses is usually non-porous inasmuch as silver is permeable to oxygen molecules.

EVALUATION

Figure 3:
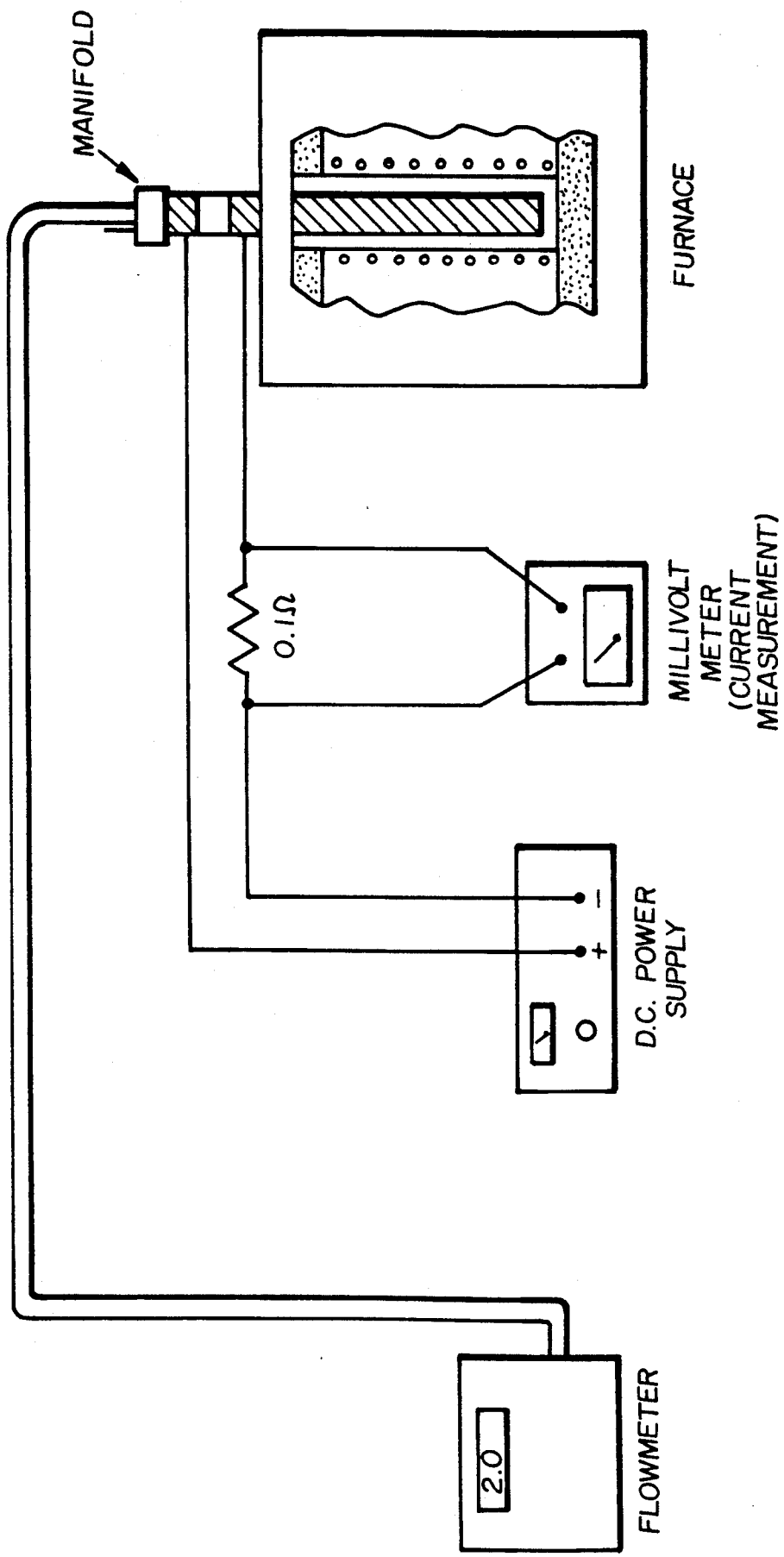
FIG. 3 is a schematic representation of an electrochemical oxygen generating system.

The completed cells are evaluated using the test setup shown schematically in FIG. 3. The setup consists of a furnace capable of operation to 800° C., a direct current (dc) power supply rated for a 0-10 volt, 100 amp output, a millivolt meter, and an instrument for measuring oxygen flow rate (either an electronic flowmeter calibrated for oxygen or a water displacement apparatus).

The cell to be evaluated is manifolded with tygon tubing to supply oxygen flow to the flow rate measurement system. Electrical contact is made in such a way as to provide a positive bias on the tube interior and a negative bias on the tube exterior. The cell is then placed into the furnace in such a way as to have an known amount of active cell area in the constant temperature zone of the furnace. The cell is heated to temperatures between 500° and 800° C. in 100° C. increments, a measurement of current density vs. voltage and oxygen flow rate being made at each temperature.

The current density is measured as a function of the applied dc voltage. Once the cell is at the temperature of interest, voltage is applied using the dc power supply and current measured by measuring the voltage drop across a 0.1 ohm resistor in series with the cell. Current is measured at 0.20, 0.50, 0.75, and 1.00 volts. Oxygen flow rate is also measured at each voltage to insure faradaic efficiency. The current density is calculated by dividing the cell current by the active cell area. In the case of the cells fabricated using this invention, the active surface area was 15.2 $cm_2$.

Figure 4:
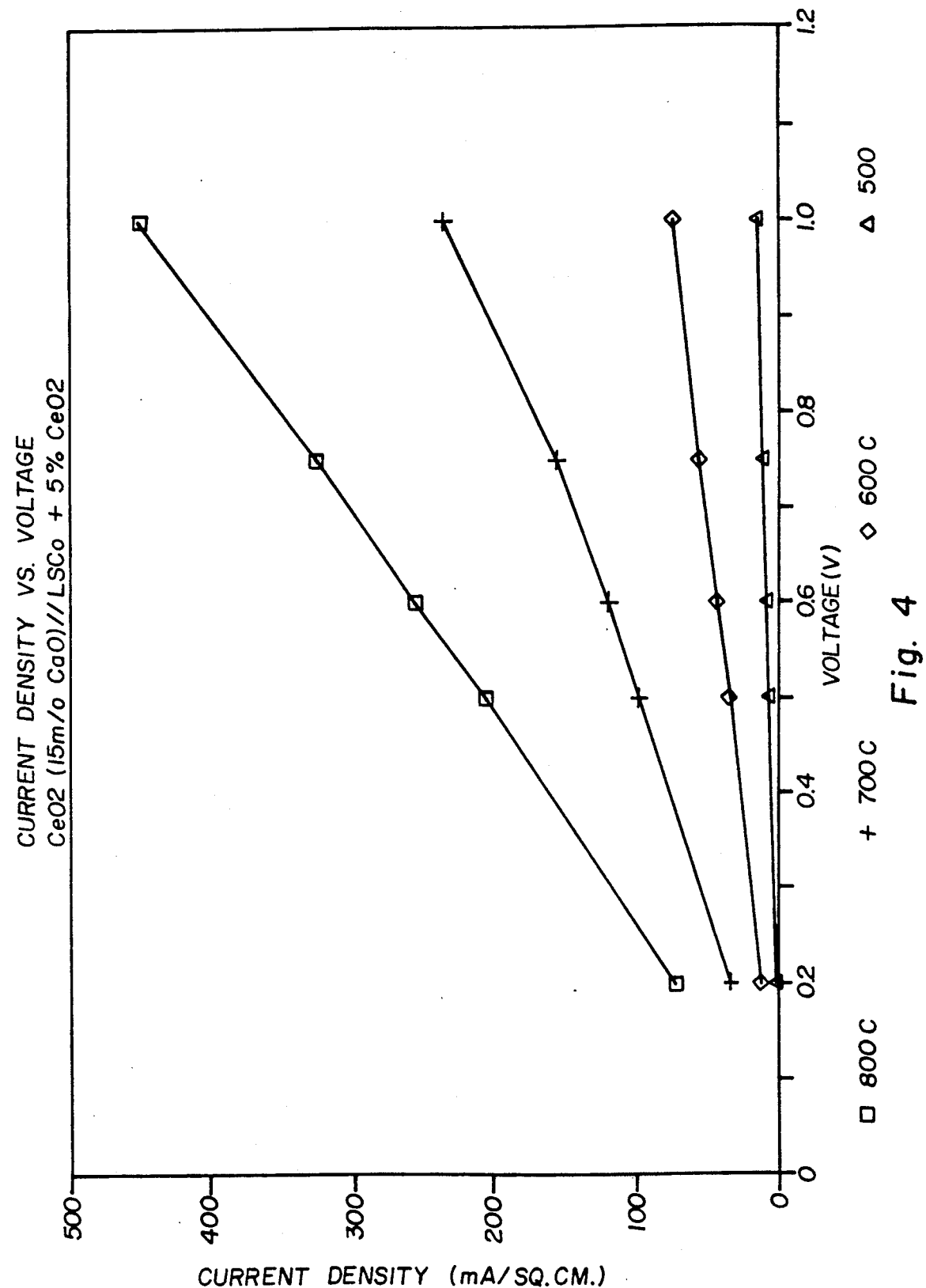
FIG. 4 is a chart illustrating the effect of temperature upon current density for a doped ceramic oxide electrolyte.
Figure 5:
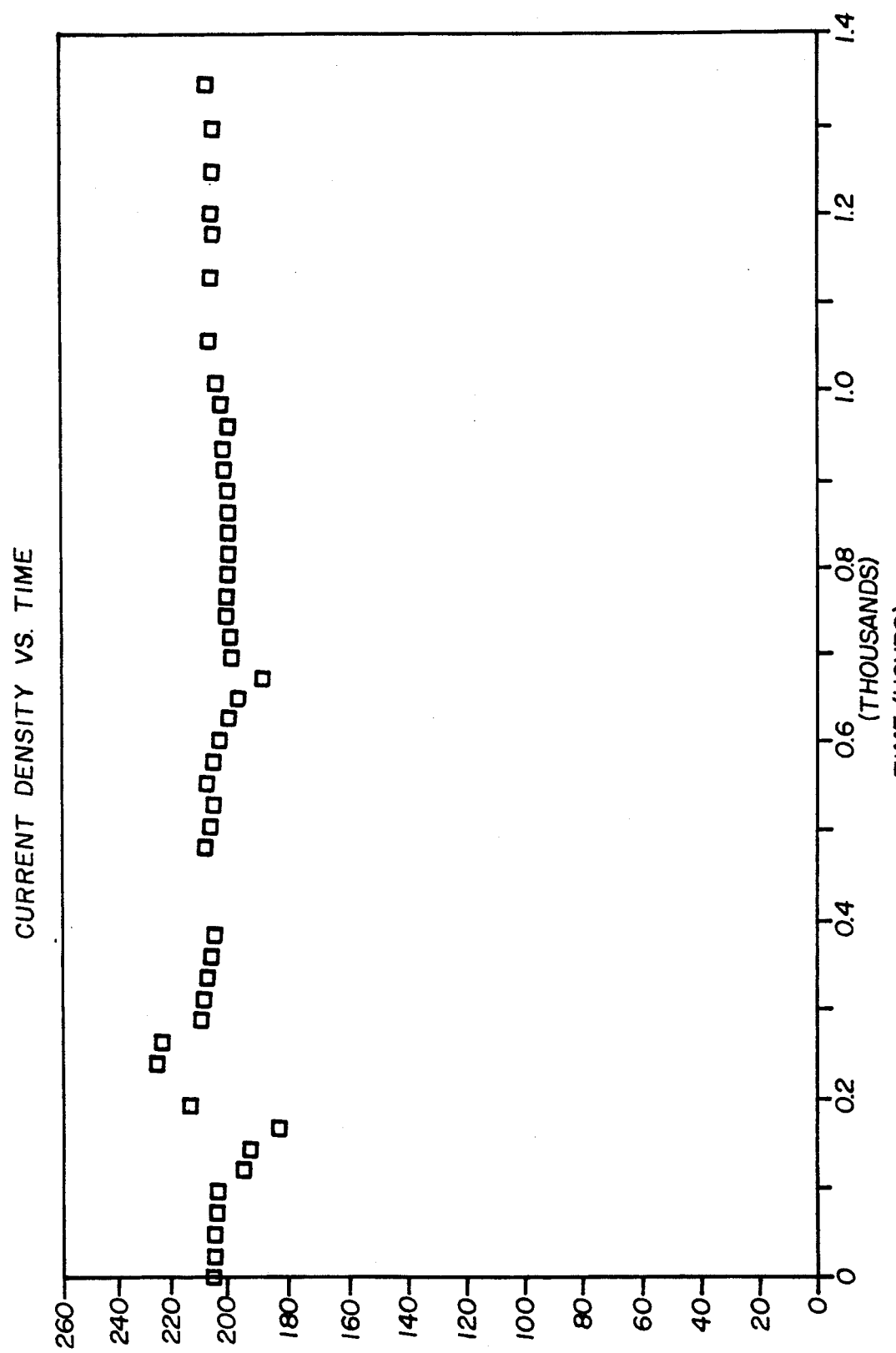
FIG. 5 is a chart showing the constancy of current density over an extended period of time for a doped cerium oxide electrolyte.

FIG. 4 shows the results of the current density vs. voltage data collected from a cell fabricated using this invention. For comparison purposes, FIG. 5 compares the current density vs. voltage characteristics at 800° C. for a cell fabricated using the existing zirconium dioxide cell technology with a cell fabricated using this invention. As can be seen in FIG. 5, the cell fabricated using this invention has a current density 290% greater than the cell fabricated using existing technology.

The electrolyte assemblies of the instant invention generally involve tubes or plates having a surface area from about 25 cm$^2$ to about 40 cm$^2$. The ceria electrolytes are formed by conventional ceramic forming techniques. The electrodes, i.e., the metal oxide materials with pervoskite crystal structure, are usually about 20 to 200 microns in thickness, although a thickness of about 70 to about 130 microns is generally preferred. The silver overcoat may be from about five to about 40 microns in thickness, although a thickness of about five to about 20 microns is generally preferred.

The silver, when applied as a very thin film, i.e., about 10±5 microns, is generally non-porous. Thicker silver films (15 microns) are generally porous. Silver is the preferred overlayer for low temperature (800° C.) operation.

Other metal overlays useful in the invention include Inconel, Monel, copper alloys, silver alloys, silver or copper-plated Inconel mesh, and the like. Overlays of materials other than silver or a silver alloy must generally contain considerable porosity.

Since there is a direct relationship between current density and the amount of oxygen produced by a device of the instant invention, a perusal of the data in FIGS. 4 and 5 illustrates the difference between oxygen delivery devices and sensors. A sensor generally operates at a current density of less than 10 milliamps while the oxygen delivery devices of this invention generally operate at a current density of at least 100 milliamps, and, as seen from FIGS. 4 and 5, current densities greater than 200 are preferred.

Automobile sensors may only operate for a period of a thousand hours. Replacement of sensors is frequently recommended after 50,000 miles. An oxygen delivery device, for example, a medical oxygen source, may require operation 24 hours/day for a year or more. The data from FIG. 5 shows continuous operation of an oxygen delivery device of the instant invention at a very high current density for a period in excess of 1400 hours.

We claim:

1. An electrolyte assembly for an electrochemical oxygen generating device consisting essentially of:
    an electrolyte comprising ceria;
    a pair of substantially continuous, porous, substantially sintered thin electrodes comprising lanthanum strontium cobaltite contacting said electrolyte; and
    an overcoat of a thin, continuous, substantially non-porous layer of silver over each of said electrodes.

2. The electrolyte assembly of claim 1 wherein said ceria is doped with an oxide selected from the class of calcium oxide, strontium oxide and yttrium oxide.

3. The electrolyte assembly of claim 1 wherein said electrodes are about 20 to about 200 microns in thickness.

4. The electrolyte assembly of claim 1 wherein said electrodes are about 70 to about 130 microns in thickness.

5. The electrolyte assembly of claim 1 wherein said silver layer is about 5 to about 15 microns in thickness.

6. The electrolyte assembly of claim 1 wherein said electrodes contain a minor quantity of ceria.

7. The electrodes of claim 1 wherein said lanthanum strontium cobaltite has the composition lanthanum oxide 0.10–0.40 moles, strontium oxide 0.20–0.80 moles, cobalt oxide 1.0 mole.

* * * * *